(12) United States Patent
Kakui et al.

(10) Patent No.: US 7,940,815 B2
(45) Date of Patent: May 10, 2011

(54) FLUORESCENT GLASS, OPTICAL WAVEGUIDE, OPTICAL FIBER, OPTICAL COHERENCE TOMOGRAPHY APPARATUS, AND OPTICAL FIBER LASER

(75) Inventors: Motoki Kakui, Yokohama (JP); Tetsuya Haruna, Yokohama (JP); Takahiro Murata, Fukuoka (JP)

(73) Assignees: Sumitomo Electric Industries, Ltd., Osaka (JP); Kyushu University, National University Corporation, Fukuoka (JP)

( * ) Notice: Subject to any disclaimer, the term of this patent is extended or adjusted under 35 U.S.C. 154(b) by 252 days.

(21) Appl. No.: 11/488,902

(22) Filed: Jul. 19, 2006

(65) Prior Publication Data

US 2007/0036509 A1    Feb. 15, 2007

(30) Foreign Application Priority Data

Jul. 19, 2005   (JP) ................ P2005-209037

(51) Int. Cl.
  *H01S 3/30*   (2006.01)
(52) U.S. Cl. .......................... 372/6; 385/142
(58) Field of Classification Search ....... 372/6; 385/142
  See application file for complete search history.

(56) References Cited

U.S. PATENT DOCUMENTS

2003/0063892 A1   4/2003   Beall et al.

FOREIGN PATENT DOCUMENTS

| JP | 11-29334 | 2/1999 |
|----|----------|--------|
| JP | 2002-068779 | 3/2002 |
| JP | 2002-252397 | 9/2002 |
| JP | 2003-283028 | 10/2003 |
| WO | WO 2006/093141 A1 | 9/2006 |

OTHER PUBLICATIONS

Fujimoto et al. "Infrared Luminescence from Bismuth-doped Silica glass", Jpn. J. Appl. Phys. vol. 40 (2001) pp. L279-L281.*
T. Suzuki et al., "Waveguides and Waveguide Materials" CTuD6, CLEO/ IQEC & PhAST Conference Program, 2004.

(Continued)

*Primary Examiner* — Tod T Van Roy
(74) *Attorney, Agent, or Firm* — McDermott Will & Emery LLP

(57) ABSTRACT

The present invention relates to fluorescent glass which is easily put into practical use, and optical elements including the same. In one aspect, the fluorescent glass is comprised of silica-based glass containing Bi as a dopant, and adapted to generate fluorescence in response to pumping light in a wavelength band of 980 nm incident thereon. In another aspect, the fluorescent glass contains at least one species of transition metal as a dopant, and exhibits a 980-nm band absorption spectrum having a full width at half maximum exceeding 10 nm. In still another aspect, the fluorescent glass is comprised of silica-based glass containing at least one species of transition element as a dopant, and exhibits a fluorescence spectrum with a peak intensity fluctuating within a range of −1 dB or more but 1 dB or less with respect to pumping light having a fixed intensity in a state set to a temperature of −5° C. or more but 65° C. or less.

10 Claims, 13 Drawing Sheets

OTHER PUBLICATIONS

T. Suzuki et al. "Room temperature broadband near-infrared emission from nickel in zinc-alumino-silicate glass" CTuD6, Optical Society of America, 2003. C. Batchelor et al., "Enhanced room-temperature emission in $Cr^{4+}$ ions containing alumino-silicate glasses" Applied Physics Letters, vol. 82, No. 23, pp. 4035-4037, 2003optical amplification Optics Letters, vol. 29, No. 17, pp. 1998-2000, 2004.

M. Peng et al., "Bismuth- and aluminum-codoped germanium oxide glasses for super-broadband optical amplification" Optics Letters, vol. 29, No. 17, pp. 1998-2000, 2004.

Japanese Notice of Reasons for Rejection, with English Translation, issued in Japanese Patent Application No. 2005-209037, dated Jan. 18, 2011.

Tetsuya Mori et al., "Compositional dependence of optical properties of $Bi_2O_3$, oxide glasses," Summary of the 41st Symposium on Basic Science of Ceramics, Jan. 22, 2009, pp. 336-337, with partial English Translation.

Xian-geng Meng et al., "Near infrared broadband emission of bismuth-doped aluminophosphate glass," Optics Express, vol. 13, No. 5, Mar. 7, 2005, pp. 1628-1634.

* cited by examiner

*Fig.1*

| SAMPLE | Bi-CONCENTRATION (wt.ppm) | Al-CONCENTRATION (wt.%) | DRAWING TEMPERATURE (°C) |
|---|---|---|---|
| A | 100 | 3.8 | 1750 |
| B | 370 | 4.2 | 1500 |

*Fig.4*

| PUMPING WAVELENGTH (nm) | PEAK WAVELENGTH (nm) | FULL-WIDTH AT HALF-MAXIMUM (nm) | COHERENCE DISTANCE ($\mu$m) |
|---|---|---|---|
| 808 | 1059 | 192 | 2.58 |
| 910 | 1107 | 161 | 3.36 |
| 976 | 1112 | 137 | 3.99 |

FLUORESCENT GLASS, OPTICAL WAVEGUIDE, OPTICAL FIBER, OPTICAL COHERENCE TOMOGRAPHY APPARATUS, AND OPTICAL FIBER LASER

BACKGROUND OF THE INVENTION

1. Field of the Invention

The present invention relates to fluorescent glass, an optical waveguide including the fluorescent glass, an optical fiber including the fluorescent glass, an optical coherence tomography apparatus including the optical waveguide, and an optical fiber laser including the optical fiber.

2. Related Background Art

Fluorescent glass doped with a laser active material generates ASE (Amplified Spontaneous Emission) by amplifying spontaneous emission (fluorescence) occurring when the laser active material pumped with pumping light returns to its ground state, or amplifies signal light by a phenomenon of stimulated emission. Examples of the laser active material added to the fluorescent glass include transition metals such as Bi, Cr, and Ni and rare-earth elements such as Er, Yb, Tm, and Nd.

The fluorescent glass generates fluorescence in a wider band when doped with a transition metal than when doped with a rare-earth element. Therefore, applying the fluorescent glass doped with transition metals to optical amplifiers which can collectively amplify a wide band of light and light sources has been under consideration. Such applied technologies are described, for example, in Documents 1 to 6 in the following:

Document 1: Japanese Patent Application Laid-Open No. 2002-252397

Document 2: Japanese Patent Application Laid-Open No. 2003-283028

Document 3: U.S. Patent Application Laid-Open No. 2003/0063892

Document 4: T. Suzuki et al., CLEO 2004, Tech. Dig., CtuD6, 2004

Document 5: C. Batchelor et al., Applied Physics Letters, Vol. 82, No. 23, pp. 4035-4037, 2003

Document 6: M. Peng et al., Optics Letters, Vol. 29, No. 17, pp. 1998-2000, 2004

The above-mentioned Documents 1, 2, and 6 describe fluorescent glass products doped with Bi. On the other hand, the above-mentioned Documents 3 to 5 disclose fluorescent glass products doped with Cr or Ni.

SUMMARY OF THE INVENTION

The inventors studied the prior art mentioned above and, as a result, have found the following problems.

The above-mentioned Document 1 discloses the use of wavelength components at 500 nm and 700 nm as pumping light for fluorescent glass, whereas the above-mentioned Document 2 discloses the use of wavelength components at 500 nm, 700 nm, and 833 nm as pumping light for fluorescent glass. Semiconductor lasers outputting light in wavelength bands of 500 nm and 700 nm are expensive and less reliable. On the other hand, adapting a semiconductor laser outputting light in a wavelength band of 800 nm to a higher output is problematic in that its transverse mode becomes multimode. Therefore, semiconductor lasers outputting light in the 800-nm wavelength band are not suitable for pumping light sources for which a higher output is required.

The fluorescent glass products disclosed in the above-mentioned Documents 3 to 5 are doped with Cr or Ni which requires temperature control in general. Therefore, temperature control is required for the fluorescent glass products to attain a stable ASE output, whereby light sources and the like employing these fluorescent glass products increase their cost.

The fluorescent glass disclosed in the above-mentioned Document 6 uses $GeO_2$-based glass instead of silica-based glass as its host glass. However, the $GeO_2$-based glass is not suitable for practical use because of its low melting point and poor reliability.

For solving the above-mentioned problems, it is an object of the present invention to provide fluorescent glass which can easily be put into practical use, an optical waveguide including the fluorescent glass, an optical fiber including the fluorescent glass, an optical coherence tomography apparatus including the optical waveguide, and an optical fiber laser including the optical fiber.

For achieving the above-mentioned object, the present invention provides fluorescent glass comprised of silica-based glass containing Bi as a dopant, and adapted to generate fluorescence in response to pumping light in a wavelength band of 980 nm incident thereon. Since the fluorescent glass generates fluorescence in response to pumping light in the wavelength band of 980 nm incident thereon, semiconductor lasers in the 980-nm wavelength band can be used as its pumping light source. The semiconductor lasers in the 980-nm wavelength band are widely used in general and thus are easily available at low cost. The reliability of such semiconductor lasers in the 980-nm wavelength band has already been verified. Bi added to the fluorescent glass emits relatively strong fluorescence in its host glass even at room temperature. Therefore, the temperature control for the fluorescent glass is easy. The foregoing makes it clear that the fluorescent glass according to the present invention can easily be put into practical use.

In the fluorescent glass according to the present invention, it will be preferred in particular if a wavelength of the pumping light and a peak wavelength of a spectrum of the fluorescence yield a difference of 16% or less with respect to the wavelength of the pumping light. In this case, the power conversion efficiency from the pumping light to ASE or laser light becomes favorable, so that the heat generated upon the power conversion is effectively suppressed.

The fluorescent glass according to the present invention may contain at least one species of transition metal as a dopant and exhibit a 980-nm band absorption spectrum having a full width at half maximum exceeding 10 nm. Since such fluorescent glass has an absorption spectrum in the 980-nm wavelength band, semiconductor lasers in the 980-nm wavelength band can be used as its pumping light source. Since the absorption spectrum exhibits a wide full width at half maximum, restrictions on choosing wavelengths of the pumping light source are alleviated. This makes it possible to choose inexpensive pumping light sources or pumping light sources with moderate temperature control.

It will be preferred in particular if the full width at half maximum exceeds 50 nm. This further alleviates the restrictions on choosing wavelengths of the pumping light source.

The fluorescent glass according to the present invention may be comprised of silica-based glass containing at least one species of transition element as a dopant, the fluorescent glass exhibiting a fluorescence spectrum with a peak intensity fluctuating within a range of −1 dB or more but 1 dB or less with respect to pumping light having a fixed intensity in a state set to a temperature of −5° C. or more but 65° C. or less. Such fluorescent glass is less dependent on temperature, and thus can easily be put into practical use.

Preferably, the optical waveguide according to the present invention comprises a core region at least partly comprised of fluorescent glass having the structure mentioned above (the fluorescent glass according to the present invention). In this case, the optical waveguide can easily be put into practical use.

Preferably, the optical fiber according to the present invention comprises a core region at least partly comprised of fluorescent glass having the structure mentioned above (the fluorescent glass according to the present invention). In this case, the optical fiber can easily be put into practical use.

The optical coherence tomography apparatus according to the present invention comprises a light source, a beam splitter, a mirror, and a photodetector, the apparatus measuring a three-dimensional tomogram of an object with a resolution of 4 μm or finer in a depth direction. Specifically, in the optical coherence tomography apparatus, the light source includes an optical waveguide having the above-mentioned structure (the optical waveguide according to the present invention), amplifies fluorescence generated by the fluorescent glass when fed with pumping light, and outputs ASE as amplified light. The beam splitter divides the ASE outputted from the light source into first divided light advancing in a first optical path direction and second divided light advancing in a second optical path direction toward an object. The mirror is arranged on an optical path of the first divided light and movable in parallel with the first optical path direction, and reflects the first divided light in a direction extending along the first optical path direction. The photodetector superposes the first divided light reflected by the mirror and the second divided light reflected by the object onto each other such that interference occurs within the beam splitter, and detects thus obtained coherent light. In the optical coherence tomography apparatus, an optical waveguide having the structure mentioned above (the optical waveguide according to the present invention) is employed in the light source outputting the ASE used for the measurement. Therefore, the optical coherence tomography apparatus can easily be put into practical use.

The optical fiber laser according to the present invention comprises an optical fiber having the structure mentioned above (the optical fiber according to the present invention), and a pumping light supply part for supplying the optical fiber with pumping light for pumping the dopant contained in the optical fiber. In particular, the optical fiber is arranged as a laser medium in an optical path of a resonator for resonating light emitted from the dopant. Since the optical fiber having the structure mentioned above (the optical fiber according to the present invention) is thus arranged as a laser medium in the optical path of the resonator, the optical fiber laser can easily be put into practical use.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 1 is a table showing the composition and drawing temperature in each of single-mode fiber samples including the fluorescent glass according to the present invention;

FIG. 4 is a table showing optical characteristics of ASE emitted from the light source in response to different wavelengths of pumping light;

DETAILED DESCRIPTION OF THE PREFERRED EMBODIMENTS

Figure 2:
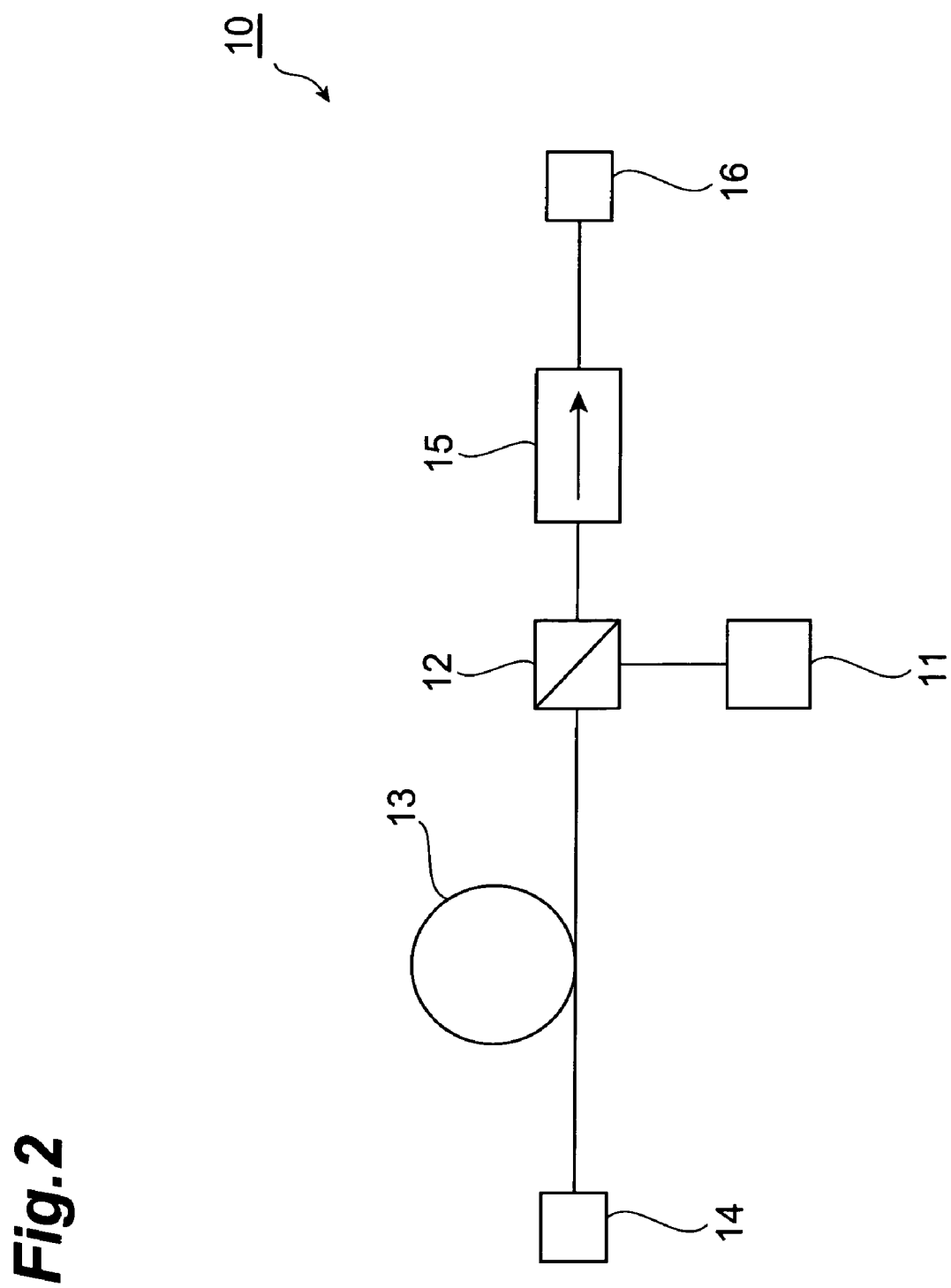
FIG. 2 is a view showing the structure of a light source employing the fluorescent glass according to the present invention.

In the following, embodiments of the present invention will be explained in detail with reference to FIGS. 1 to 13. In the explanation of the drawings, constituents identical to each other will be referred to with numerals identical to each other without repeating their overlapping descriptions.

To begin with, a first embodiment of the fluorescent glass according to the present invention will be explained. The fluorescent glass according to the first embodiment is silica-based glass containing Bi as a dopant, and is pumped with pumping light in a wavelength band of 980 nm, so as to generate fluorescence. Preferably, in the fluorescent glass according to the first embodiment, the difference between the wavelength of pumping light and a peak wavelength of a fluorescence spectrum is 16% or less with respect to the wavelength of pumping light.

The fluorescent glass according to the first embodiment is pumped with pumping light in the 980-nm wavelength band. Therefore, a semiconductor laser in the 980-nm wavelength band can be used as a pumping light source. Semiconductor lasers in the 980-nm wavelength band are widely used for Er-doped fiber amplifiers (EDFA), and thus are inexpensive and highly reliable.

The fluorescent glass according to the first embodiment contains Bi as a dopant. As compared with rare-earth elements such as Er, Yb, Tm, and Nd, Bi emits fluorescence over a remarkably wider band. Therefore, the fluorescent glass containing Bi can emit fluorescence over a wide band. In addition, Bi emits strong fluorescence in host glass even at room temperature. Therefore, the fluorescent glass is easy to control in terms of temperature. The foregoing makes it clear that the fluorescent glass according to the first embodiment can easily be put into practical use.

When the difference between the wavelength of pumping light and a peak wavelength of a fluorescence spectrum is 16% or less with respect to the wavelength of pumping light, the difference in photon energy between the pumping light and ASE is small, while the power conversion efficiency from the pumping light to ASE or laser light becomes favorable. When fluorescent glass having such a favorable power conversion efficiency is employed in an optical amplifier waveguide, heat is effectively restrained from occurring upon the conversion. The optical amplifier waveguide or the like having suppressed the heat generation therewithin can favorably be employed in a high-output laser or amplifier of several hundreds of watts or several kilowatts used for laser processing.

A second embodiment of the fluorescent glass according to the present invention will now be explained. The fluorescent glass according to the second embodiment contains at least one species of transition metal as a dopant, and exhibits a 980-nm band absorption spectrum having a full width at half maximum exceeding 10 nm. More preferably, in the fluorescent glass according to the second embodiment, the full width at half maximum of the 980-nm band absorption spectrum exceeds 50 nm.

The fluorescent glass according to the second embodiment has an absorption spectrum in the 980-nm wavelength band. Therefore, a semiconductor laser in the 980-nm wavelength band can be employed as a pumping light source. As mentioned above, semiconductor lasers in the 980-nm wavelength band are inexpensive and highly reliable.

The fluorescent glass according to the second embodiment contains a transition metal as a dopant. As compared with rare-earth elements such as Er, Yb, Tm, and Nd, transition elements such as Bi, Cr, and Ni emit fluorescence over a remarkably wider band. Therefore, the fluorescent glass can emit fluorescence over a wide band.

The absorption spectrum of the fluorescent glass according to the second embodiment has a broad full width at half maximum exceeding 10 nm. Therefore, restrictions on choosing the wavelength of the pumping light source are low. For example, inexpensive pumping light sources or light sources with low demand for temperature control can be chosen. Using a pumping light source under moderate temperature control further reduces the cost and power consumption required for temperature control. In addition, the pumping light power can be improved by wavelength division multiplexing (WDM) of pumping light in the 980-nm band, which is not easy in EDFA. Restrictions on choosing the wavelength of the pumping light source become lower in the case of fluorescent glass having an absorption spectrum with a full width at half maximum exceeding 50 nm. The foregoing makes it clear that the fluorescent glass according to the second embodiment can easily be put into practical use.

A third embodiment of the fluorescent glass according to the present invention will now be explained. The fluorescent glass according to the third embodiment is silica-based glass containing at least one species of transition element as a dopant, and exhibits a fluorescence spectrum with a peak intensity fluctuating within a range of −1 dB or more but 1 dB or less with respect to pumping light having a fixed intensity in a state set to a temperature of −5° C. or more but 65° C. or less.

The fluorescent glass according to the third embodiment contains at least one species of transition element as a dopant, whereas the transition metal emits fluorescence over a much wider band than rare-earth elements do as mentioned above. Therefore, the fluorescent glass can emit fluorescence over a wide band.

However, the temperature dependency of the fluorescence spectrum emitted from a transition element is hard to consider favorable in general. Nevertheless, the fluorescent glass according to the third embodiment set to a temperature of −5° C. or more but 65° C. or less can be employed for communications, for example, since the fluctuation of the peak intensity in the fluorescence spectrum with respect to pumping light having a fixed intensity falls within the range of −1 dB or more but 1 dB or less. The foregoing makes it clear that the fluorescent glass according to the third embodiment can easily be put into practical use.

Single-mode fiber (SMF) samples A and B each having a core part including fluorescent glass containing transition metal Bi will now be explained. Each of samples A and B is a Bi-doped silica-based fiber (BiDF) co-doped with Al. FIG. 1 shows the compositions of samples A and B and their temperatures in a furnace at the time of fiber drawing in the final stage of manufacture.

Sample A employed silica-based glass as a host material, and was doped with 100 wt.ppm of Bi element ion and co-doped with 3.8 wt. % of Al element ion. Sample B employed silica-based glass as a host material, and was doped with 370 wt.ppm of Bi element ion and co-doped with 4.2 wt. % of Al element. Each of samples A and B was manufactured by the same equipment (at a drawing rate of 50 m/second) as with Er-doped optical fibers (EDF) for communications. The drawing temperatures for samples A and B were 1750° C. and 1500° C., respectively. Each of samples A and B was manufactured by very rapid cooling such that it took 1 second or less to solidify from a molten state.

Results of measurement of ASE emitted from respective light sources including samples A and B will now be explained. FIG. 2 is a view showing the structure of a light source including sample A or B. The light source shown in FIG. 2 comprises a pumping light source 11, a WDM coupler 12, an optical fiber 13, a resistive terminator (SME) 14, an optical isolator 15, and an output connector 16. Sample A or B having a length of 5 m is employed as the optical fiber 13. The light source 10 is of backward pumping type. Therefore, ASE is outputted so as to advance through sample A or B in a direction opposite from pumping light.

The pumping light source 11 outputs the pumping light toward the WDM coupler 12. The WDM coupler 12 reflects the pumping light outputted from the pumping light source 11 so as to guide it to the optical fiber 13, and transmits therethrough the ASE outputted from the optical fiber 13 to the optical isolator 15. When the optical fiber 13 is fed with the pumping light outputted from the pumping light source 11, the dopant added to the optical fiber 13 attains an excited state. The dopant added to the optical fiber 13 generates spontaneous emission (fluorescence) when returning to the ground state from the excited state. The optical fiber 13 amplifies the spontaneous emission (fluorescence) and outputs the resulting ASE. The optical isolator 15 transmits therethrough the ASE outputted from the optical fiber 13 toward the output connector 16, but does not transmit light therethrough in the opposite direction.

For measuring the ASE outputted from the light source 10, three kinds of pumping light at wavelengths of 808 nm, 910 nm, and 976 nm were used. The pumping power was 185 mW in each measurement.

Figure 3:
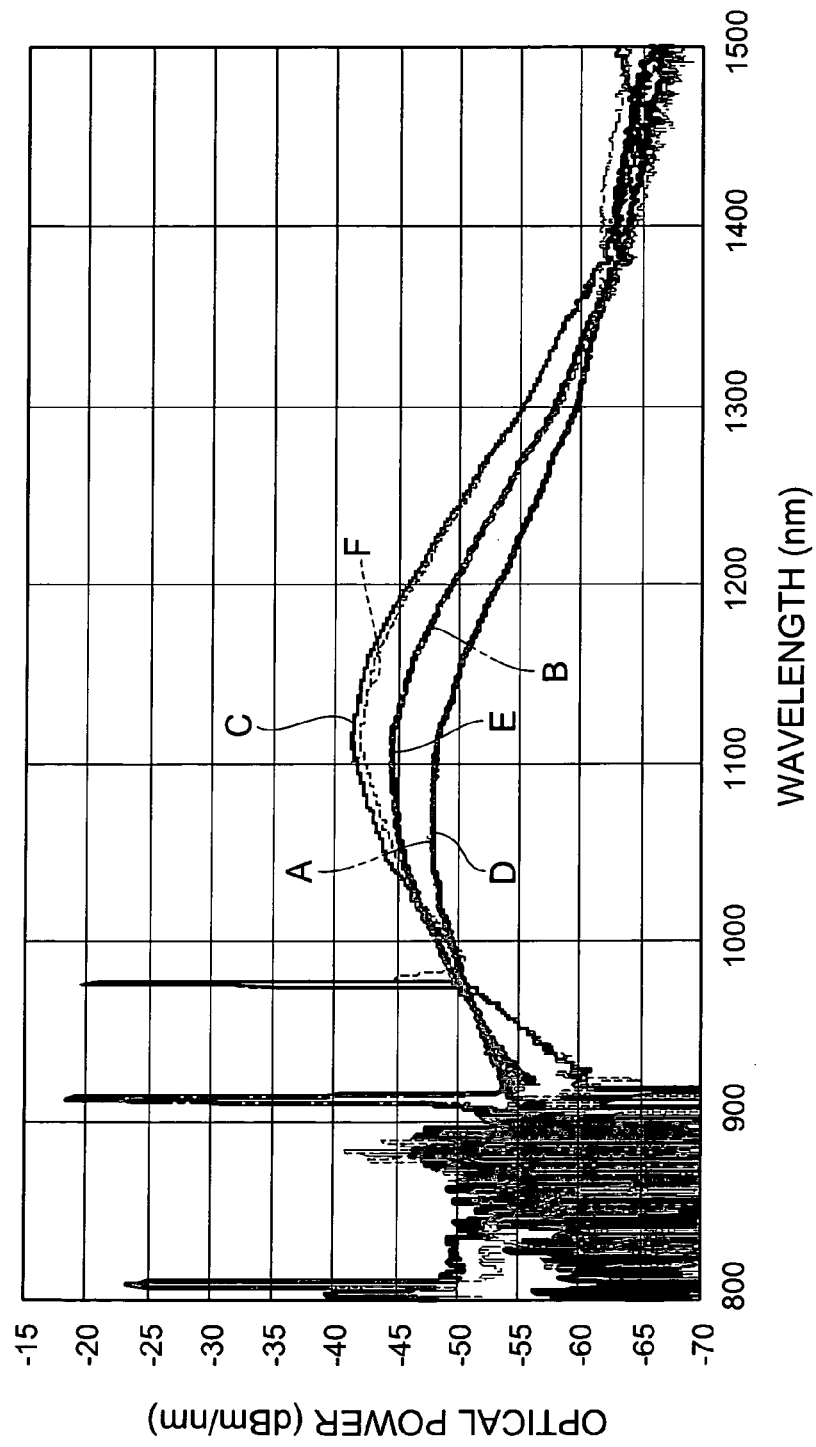
FIG. 3 is a chart showing spectra of ASE outputted from the light source including the fluorescent glass shown in FIG. 2.

FIG. 3 shows ASE spectra outputted from the light source 10 including sample A or B (FIG. 2) when the wavelengths 808 nm, 910 nm, and 976 nm of pumping light were supplied. In FIG. 3, the abscissa indicates the wavelength (nm) of ASE, whereas the ordinate indicates the optical power (dBm/nm) of ASE. In FIG. 3, spectrum A is the ASE spectrum of the light source 10 including sample A pumped with the pumping light at the wavelength of 808 nm, spectrum B is the ASE spectrum of the light source 10 including sample A pumped with the pumping light at the wavelength of 910 nm, spectrum C is the ASE spectrum of the light source 10 including sample A pumped with the pumping light at the wavelength of 976 nm, spectrum D is the ASE spectrum of the light source 10 including sample B pumped with the pumping light at the wavelength of 808 nm, spectrum E is the ASE spectrum of the light source 10 including sample B pumped with the pumping light at the wavelength of 910 nm, and spectrum F is the ASE spectrum of the light source 10 including sample B pumped with the pumping light at the wavelength of 976 nm. The spectra of ASE shown in FIG. 3 were corrected for the insertion losses of the WDM coupler 12 and isolator 15 inserted for multiplexing the pumping light.

As can be seen from FIG. 3, the ASE spectrum of the light source 10 including sample A has substantially the same form as with the ASE spectrum of the light source 10 including sample B at any pumping wavelength. Namely, spectra A and D have substantially the same form, spectra B and E have substantially the same form, and spectra C and F have substantially the same form.

FIG. 3 further makes it clear that the ASE spectra of the light source 10 including sample A and the ASE spectra of the light source 10 including sample B have different peak wavelengths and peak values depending on the pumping wavelengths. Namely, the set of spectra A and D, the set of spectra B and E, and the set of spectra C and F have different peak wavelengths and peak values. Specifically, the ASE spectra (spectra C and F) obtained when pumped with the pumping light at the wavelength of 976 nm have a peak value greater by 6 dB or more than that in the ASE spectra (spectra A and D) obtained when pumped with the pumping light at the wavelength of 808 nm.

Each of the peak values of spectra A to F is greater by 1 digit in terms of absolute value than the peak values of ASE spectra shown in FIGS. 1 to 3 in Document 3. When the fluorescent glass products disclosed in Documents 1, 2, and 6 are pumped with the pumping light at the wavelength of 808 nm, their ASE spectra exhibit a peak wavelength within the O band (1260 nm to 1360 nm). By contrast, each of the light source 10 including sample A and the light source 10 including sample B exhibits an ASE spectrum whose peak wavelength exists near the band of 1100 nm even when pumped with the pumping light at the wavelength of 808 nm. Each of the fluorescent glass products disclosed in Documents 1, 2, and 6 exhibits an ASE spectrum whose full width at half maximum is 300 nm or more. In contrast, the full width at half maximum is 200 nm or less in both of the light source 10 including sample A and the light source 10 including sample B.

FIG. 4 shows the wavelength (center wavelength) of each pumping light at its peak, ASE peak wavelength $\lambda_c$, ASE full width at half maximum $\Delta v$, and coherence distance for each of the ASE emitted from the light source 10 including sample A and the ASE emitted from the light source 10 including sample B. Using the ASE peak wavelength $\lambda_c$ and ASE full width at half maximum $\Delta v$, the coherence distance p is given by the following expression (1):

$$p = (2 \cdot \ln(2) \cdot \pi) \cdot (\lambda_c^2 / \Delta \lambda) \quad (1)$$

FIG. 3 also makes it clear that the peak wavelength of the fluorescent spectrum with respect to the pumping wavelength in the 976-nm band is 1112 nm. In this case, the ratio (hereinafter simply referred to as power conversion ratio) of the difference (136 nm) between the pumping light wavelength (976 nm) and the peak wavelength of the fluorescence spectrum (1112 nm) with respect to the pumping light wavelength is about 14%. By contrast, an optical fiber (YbDF) doped with rare-earth Yb and suitable for high-output lasers, amplifiers, and the like usually yields fluorescence having a wavelength of 1064 nm or longer with respect to pumping light in the 915-nm wavelength band. The power conversion ratio exceeds 16% in this case. Therefore, BiDF seems to be more suitable for purposes requiring higher output as compared with YbDF from the viewpoint of photon energy.

The absorption spectrum of YbDF also exhibits a main peak near 975 nm, thereby yielding an excellent power conversion ratio of about 9%. However, the form of the 975-nm band absorption spectrum in YbDF has been considered so sharp (with a full width at half maximum of 10 nm or less) that performances drastically change when wavelength shifts are generated by temperature changes of the pumping light source and the like.

Each of the Bi-doped fluorescent glass products disclosed in Documents 1, 2, and 6 emits fluorescence having a wavelength of 1250 nm or longer with respect to pumping light at the wavelength of 800 nm. In this case, the power conversion ratio is 50% or higher, which is unsuitable for achieving higher output.

Figure 5:
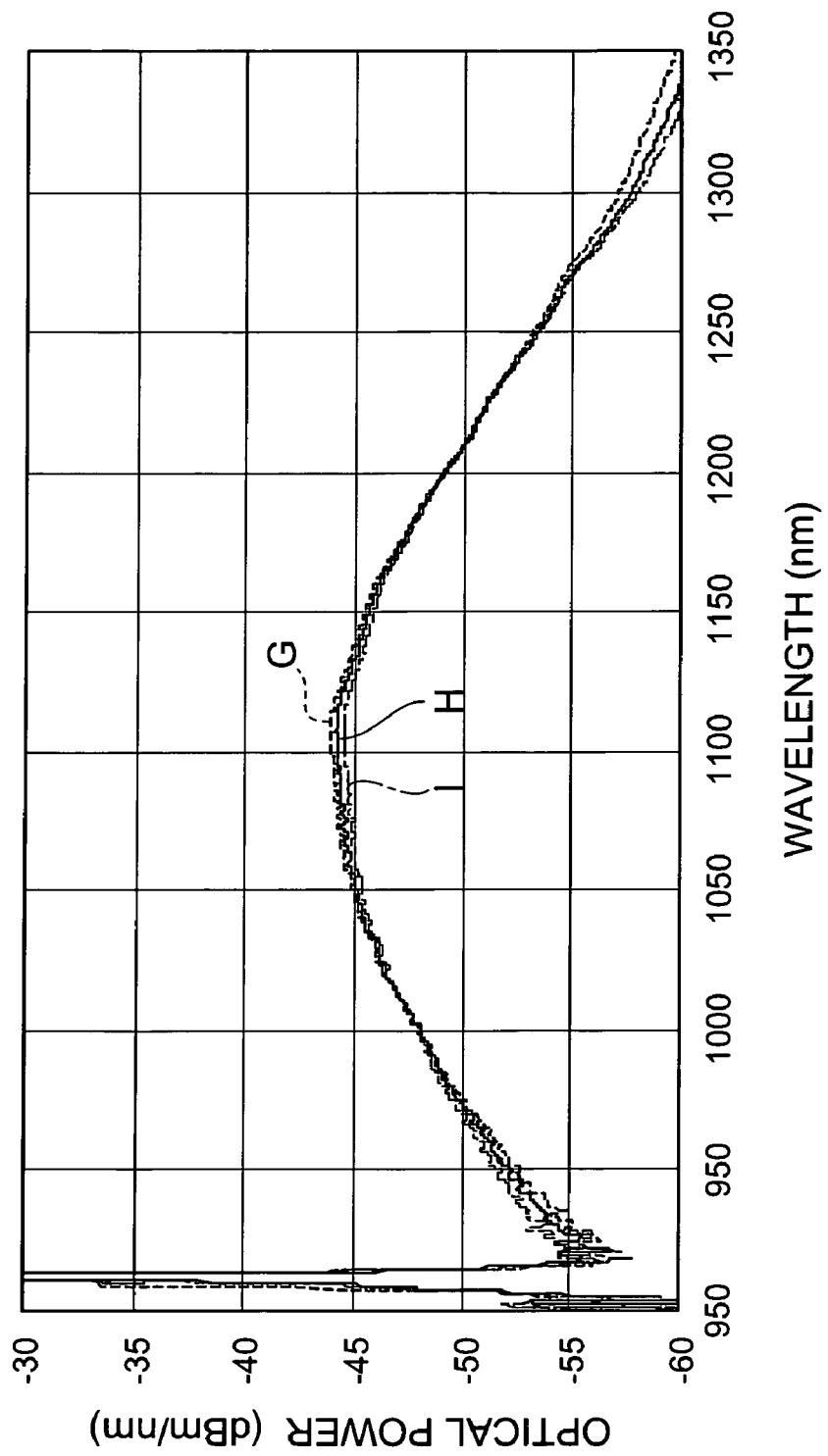
FIG. 5 is a chart showing ASE spectra obtained when the ambient temperature of an optical fiber is varied.

FIG. 5 shows ASE spectra emitted from the light source 10 shown in FIG. 2 when only the part of optical fiber 13 in the light source 12 is accommodated in a thermostat while the temperature within the thermostat is changed within the range of −20° C. to 85° C. FIG. 5 shows the results of measurement obtained when using sample A as the optical fiber 13 and pumping sample A with pumping light having a wavelength of 910 nm and a pumping power of 185 mW. In FIG. 5, the abscissa and ordinate indicate the wavelength (nm) and optical power (dBm/nm) of ASE, respectively. In FIG. 5, spectra G, H, and I are ASE spectra at −20° C., 25° C., and 85° C., respectively.

As can be seen from FIG. 5, the peak fluctuation of ASE spectra falls within the range of −0.3 dB to +3 dB within a temperature difference range of 100° C. or more from −20° C. to 85° C. For communication purposes, temperature dependency is evaluated within the temperature range of −5° C. to 65° C. in general. As shown in FIG. 5, sample A exhibits ASE spectra whose peak fluctuations fall within the range of −0.2 dB to +0.2 dB at −5° C. to 65° C. (with a low temperature dependency), and thus is considered sufficiently tolerable for communication purposes. For processing apparatus and medical apparatus, temperature dependency is evaluated in a temperature range narrower than that used for communication purposes. Consequently, sample A has a temperature characteristic sufficiently tolerable for not only communication purposes, but also processing and medical purposes, and is expected to operate stably (can easily be put into practical use).

Figure 6:
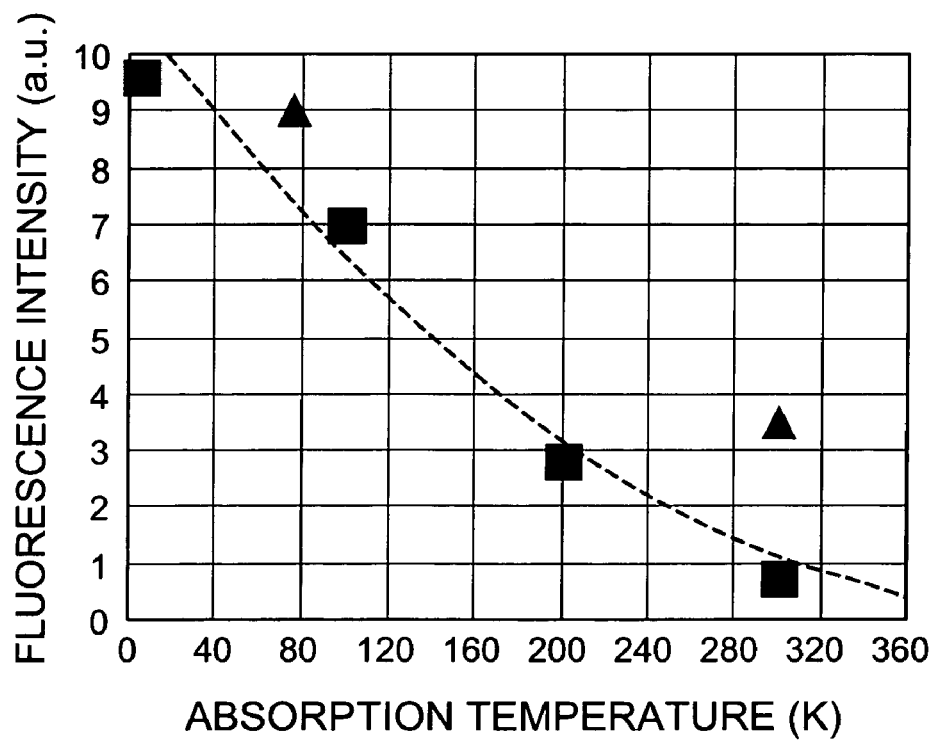
FIG. 6 is a graph showing temperature dependencies of peak values in fluorescence spectra of fluorescent glass products.

In general, fluorescence emitted from a transition metal is highly dependent on temperature, and thus is hard to keep its temperature environment. FIG. 6 shows temperature dependencies of peak values in fluorescence spectra of the fluorescent glass products disclosed in Documents 4 and 5. In FIG. 6, the abscissa and ordinate indicate the absolute temperature (K) and fluorescence intensity (a.u.), respectively. Triangle symbols indicate temperature dependencies of the Ni-doped fluorescent glass disclosed in Document 4, whereas square symbols indicate temperature dependencies of the Cr-doped fluorescent glass disclosed in Document 5. The dotted line is an interpolated curve for the temperature dependencies of the Ni-doped fluorescent glass disclosed in Document 4 as indicated by the triangle symbols.

In the Ni-doped fluorescent glass disclosed in Document 4, as shown in FIG. 6, the fluorescence intensity at −20° C. (≈253 K) is about 1.7 times (2.4 dB) that at room temperature, whereas the fluorescence intensity at 85° C. (≈358 K) is about 0.37 times (4.6 dB) that at room temperature. The fluorescent glass having such a high temperature dependency is hard to put into practical use.

Figure 7:
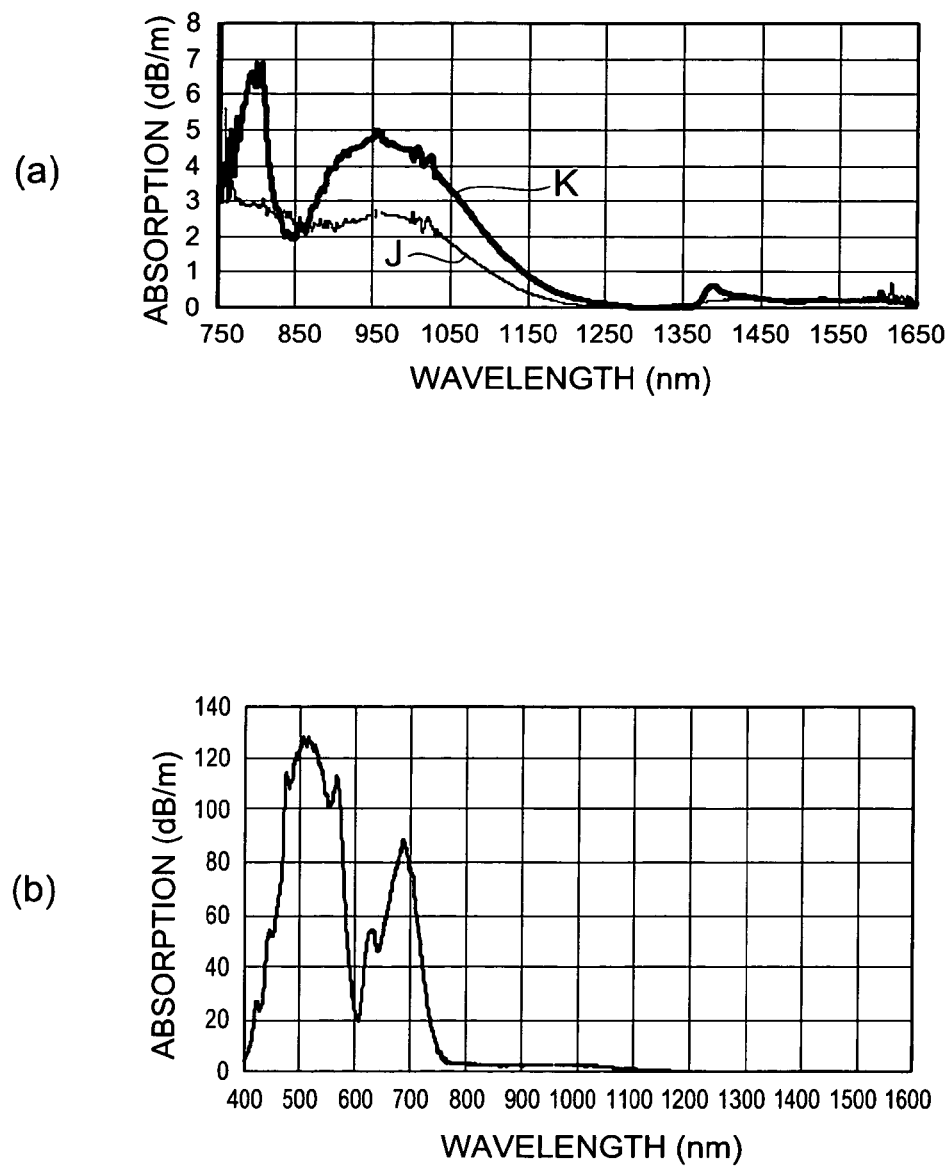
FIG. 7 is a chart showing absorption spectra of fluorescent glass.

FIG. 7 shows absorption spectra of samples A and B. In particular, the area (a) of FIG. 7 shows respective absorption spectra of samples A and B in a wavelength region of 750 nm or more, whereas the area (b) shows the absorption spectrum of sample A. In each of the areas (a), (b) shown in FIG. 7, the abscissa and ordinate indicate the wavelength and absorption coefficient, respectively. In the area (a) shown in FIG. 7, spectra J and K are respective absorption spectra of samples A and B.

As can be seen from the area (a) shown in FIG. 7, sample B shows a peak more remarkable than that of sample A. This seems to be because of the fact that the Bi concentration is higher in sample B than in sample A. Further, the area (a) shown in FIG. 7 makes it clear that both of the respective absorption spectra of samples A and B have moderate peaks centered at the wavelength of 950 nm. By contrast, the absorption spectra of the fluorescent glass products disclosed in Documents 1 and 2 have no peak in the 950-nm wavelength band. Therefore, unlike the fluorescent glass products disclosed in Documents 1 and 2, samples A and B can use 980-nm band laser diodes as their pumping light sources. The 980-nm band laser diodes are widely used as Er-doped fiber amplifiers (EDFA), and thus are inexpensive, while their reliability has already been fully verified.

Figure 8:
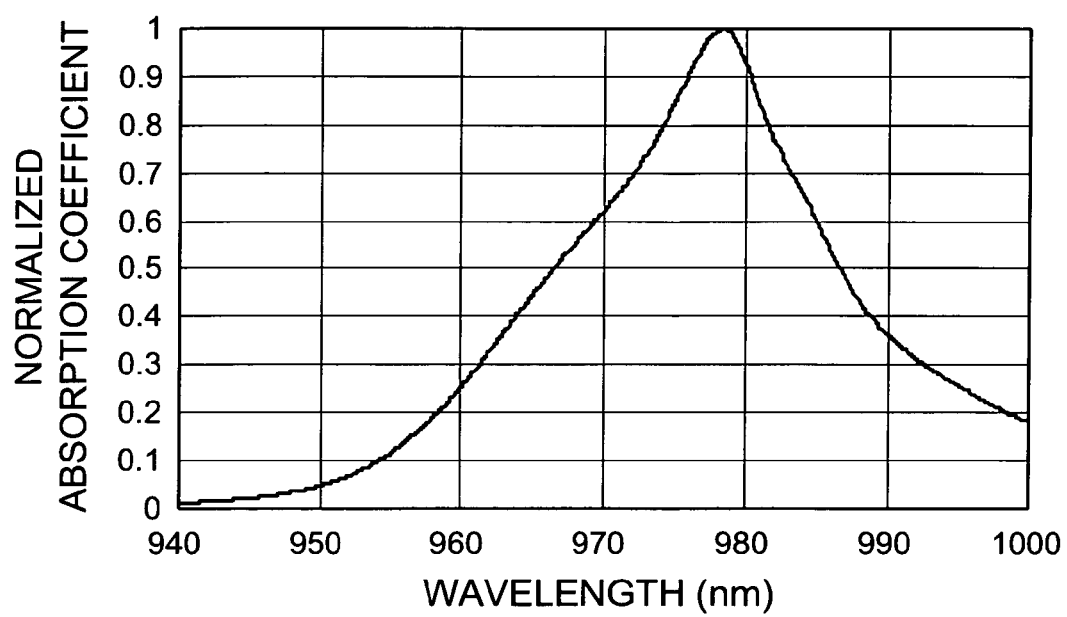
FIG. 8 is a chart showing a 980-nm band absorption spectrum of an EDF (Er-Doped Fiber)

Spectrum K in the area (a) of FIG. 7 makes it clear that the full width at half maximum in the 950-nm band absorption spectrum of sample B reaches 200 nm. FIG. 8 shows the 980-nm band absorption spectrum of an Er-doped optical fiber (EDF). As can be seen FIG. 8, the full width at half maximum in the 950-nm band absorption spectrum of the EDF is about 20 nm. Since the absorption spectrum of sample B has such a broad full width at half maximum, the wavelength of the pumping light source for sample B can be chosen under a moderate condition.

Figure 9:
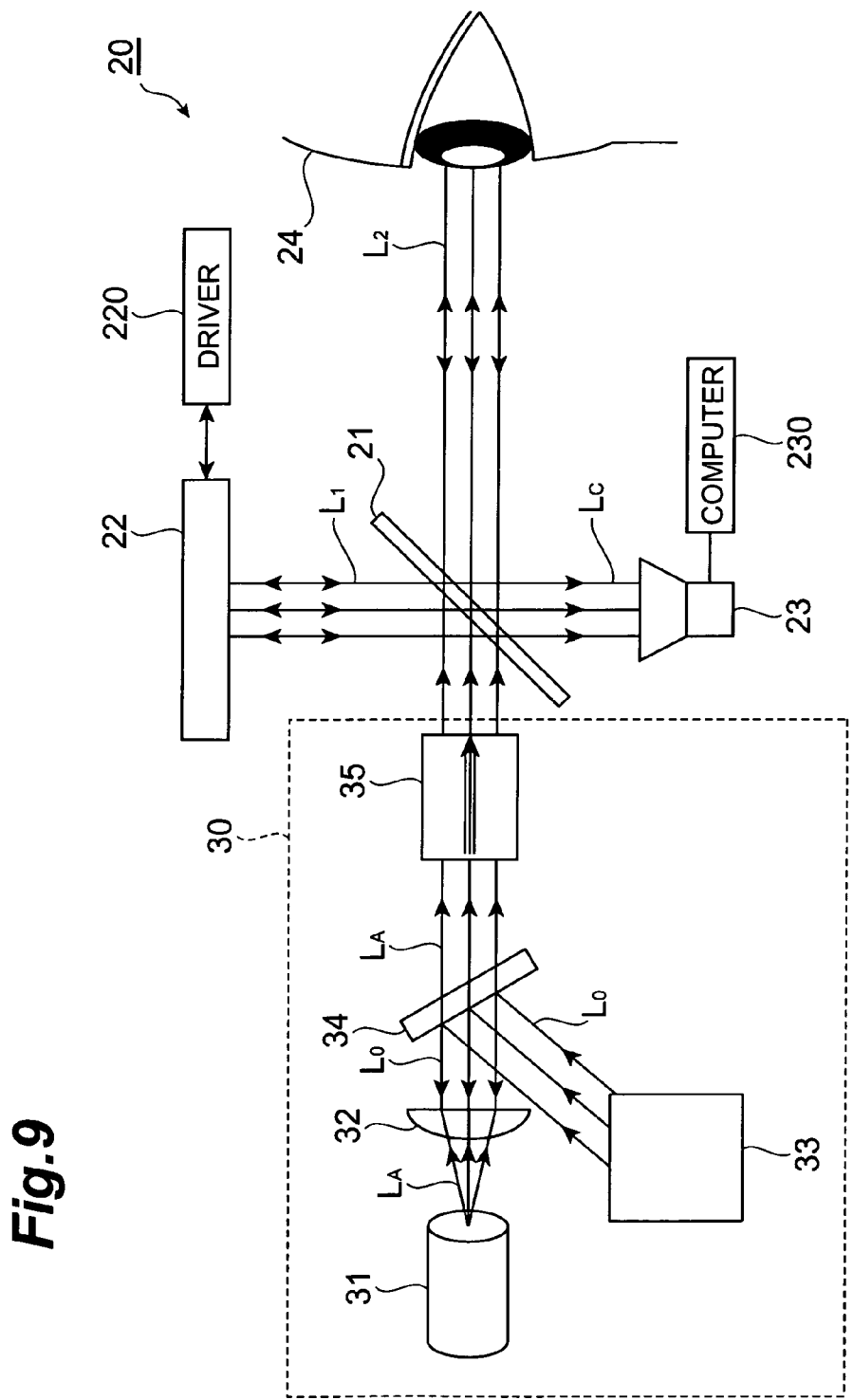
FIG. 9 is a view showing a structure of the optical coherence tomography apparatus (OCT apparatus) according to the present invention.

An embodiment of the OCT apparatus according to the present invention will now be explained. FIG. 9 is a view showing the structure of an embodiment of the OCT apparatus according to the present invention. The OCT apparatus shown in FIG. 9 comprises a light source 30, a beam splitter 21, a mirror 22, and a photodetector 23, and is an apparatus for attaining a three-dimensional tomogram of an object 24. The principle of measurement by the OCT apparatus 20 will be explained in brief. ASE $L_A$ outputted from the light source 30 is initially split into two by the beam splitter 21, whereas thus divided light components illuminate the mirror 22 and object 24, respectively. The two divided light components respectively reflected by the mirror 22 and object 24 are superposed on each other within the beam splitter 21, whereby coherent light $L_C$ is obtained. The coherent light $L_C$ is detected by the photodetector 23, and thus detected signal is turned into a tomogram by a computer or the like, whereby a three-dimensional tomogram of the object 24 is obtained.

The light source 30 comprises an optical waveguide 31 in which fluorescent glass having the structure mentioned above (the fluorescent glass according to the present invention) is employed in at least a core region thereof, and a pumping light source 33 for supplying pumping light $L_0$ to the fluorescent glass in the optical waveguide 31. The light source 30 further comprises a lens 32, a WDM filter 34, and an optical isolator 35. The light source 30 is of backward pumping type as shown in FIG. 9. Therefore, the light source 30 emits the ASE $L_A$ so as to make it advance in a direction opposite from the pumping light $L_0$ from the end face of the optical waveguide 31 where the pumping light $L_0$ is incident.

To the WDM filter 34, the pumping light source 33 outputs the pumping light $L_0$ having a wavelength (e.g., 980 nm) which can pump the dopant added to the optical waveguide 31. The WDM filter 34 reflects the pumping light $L_0$ toward the optical waveguide 31, and transmits therethrough the ASE $L_A$ outputted from the optical waveguide 31 toward the optical isolator 35. The optical waveguide 31 outputs the ASE $L_A$ when fed with the pumping light $L_0$ outputted from the pumping light source 33. The lens 32 converges the pumping light $L_0$ onto the end face of the optical waveguide 31, and collimates the ASE $L_A$ outputted from the optical waveguide 31. The optical isolator 35 transmits therethrough the ASE $L_A$ outputted from the optical waveguide 31 in the direction from the WDM filter 34 to the beam splitter 21, but does not transmit light in the opposite direction.

The beam splitter 21 arranged on the optical path of the ASE $L_A$ reflects a part of the ASE $L_A$ and transmits the remainder therethrough. The beam splitter 21 divides the ASE $L_A$ into first divided light $L_1$ and second divided light $L_2$. The first divided light $L_1$ is the part of ASE $L_A$ reflected by the beam splitter 21, and advances along a first optical path direction which intersects the optical path of the ASE $L_A$. The second divided light $L_2$ is the part of ASE $L_A$ transmitted through the beam splitter 21, and advances toward the object 24 along a second optical path direction which is parallel to the optical path of the ASE $L_A$. The beam splitter 21 superposes the first divided light $L_1$ reflected by the mirror 22 and the second divided light $L_2$ reflected by the object 24 onto each other, thereby generating coherent light.

The mirror 22 reflecting the first divided light $L_1$ is placed on the optical path of the first divided light $L_1$. The mirror 22 is arranged such as to reflect the first divided light $L_1$ in a direction extending along the first optical path direction. The mirror 22 is held by a driver 220 so as to be movable in parallel with the first optical path direction.

On the other hand, the object 24, which is a reflector reflecting the second divided light $L_2$, is arranged on the optical path of the second divided light $L_2$.

The photodetector 23 detects the coherent light $L_C$ obtained by superposing the first divided light $L_1$ and the second divided light $L_2$ onto each other within the beam splitter 21. The OCT apparatus 20 is equipped with a computer 230 for turning the detected coherent light $L_C$ into a tomogram, and attains a three-dimensional tomogram of the object 24 with a resolution of 4 μm or finer in the depth direction.

Operations of the OCT apparatus 20 will now be explained. The pumping light $L_0$ outputted from the pumping light source 33 is supplied to the optical waveguide 31 by way of the WDM filter 34 and lens 32. The pumping light $L_0$ supplied to the optical waveguide 31 pumps the dopant contained in the optical waveguide 31. The spontaneous emission (fluorescence) generated when the pumped dopant returns to its ground state is amplified in the optical waveguide 31, so as to yield the ASE $L_A$. The ASE $L_A$ generated in the optical waveguide 31 is outputted from the optical waveguide 31 along the entrance optical path of the pumping light $L_0$. Thus outputted ASE $L_A$ successively passes the lens 32, WDM filter 34, and optical isolator 35, so as to be made incident on the beam splitter 21.

The ASE $L_A$ incident on the beam splitter 21 is split thereby into two, i.e., the first divided light $L_1$ and second divided light $L_2$. The first divided light $L_1$, which is the part of ASE reflected by the beam splitter 21, is made incident on the mirror 22. The mirror 22 reflects the first divided light $L_1$ in a direction extending along the first optical path direction which is the same direction as with its entrance optical path, whereby the first divided light $L_1$ returns to the beam splitter 21. On the other hand, the second divided light $L_2$, which is the part of ASE transmitted through the beam splitter 21, advances toward the object 24 and illuminates the same. The second divided light $L_2$ illuminating the object 24 propagates through the object 24 while causing forward/backward scattering. In the scattered light having propagated through the object 24 as such, backscattered light is made incident on the beam splitter 21, so as to be superposed on the first divided light $L_1$ reflected by the mirror 22.

The photodetector 23 detects the coherent light $L_C$ obtained by superposing the first divided light $L_1$ and the second divided light $L_2$ onto each other. As an interference signal, only the backscattered light from a point within the object 24 which is separated from the beam splitter 21 by the distance between the beam splitter 21 and mirror 22 is selectively detected by the photodetector 23. Here, the mirror 22 is movable in directions extending along the first optical path direction that is the same direction as the optical path of the first divided light $L_1$. When the driver 220 moves the mirror 22, a scattering point at which the interference signal is detected within the object 24 can be chosen along the optical axis of the second divided light $L_2$. Namely, moving the mirror 22 makes it possible to scan the measurement point in the depth direction of the object 24. The interference signal detected by the photodetector 23 is thereafter processed by the computer 230 and the like, whereby a tomogram of the object 24 is obtained.

The light source 30 comprises fluorescent glass having the structure mentioned above (the fluorescent glass according to the present invention). Therefore, 980-nm wavelength band semiconductor lasers which are inexpensive and highly reliable can be used as the pumping light source 33 when the optical waveguide 31 includes silica-based fluorescent glass, adapted to generate fluorescence in response to pumping light in the 980-nm wavelength band, containing Bi as a dopant. Since the fluorescent glass contains Bi, the temperature control for the optical waveguide 31 is easy.

The 980-nm wavelength band semiconductor lasers, which are inexpensive and highly reliable, can also be used as the pumping light source when the optical waveguide 31 includes fluorescent glass containing at least one species of transition metal as a dopant and having a 980-nm band absorption spectrum whose full width at half maximum exceeds 10 nm. In addition, this alleviates restrictions on choosing the wavelength of the pumping light source.

When the optical waveguide 31 includes silica-based fluorescent glass containing at least one species of transition metal and exhibiting a fluorescence spectrum with a peak intensity fluctuating within a range of −1 dB or more but 1 dB or less with respect to pumping light having a fixed intensity in a state set to a temperature of −5° C. or more but 65° C. or less, its temperature dependency becomes lower, so that it can easily be put into practical use.

As in the foregoing, the OCT apparatus 20 can easily be put into practical use when equipped with the light source 30 including the fluorescent glass according to the present invention.

In general, superluminescent diodes (hereinafter simply referred to as SLD) have been in use as light sources in OCT apparatus. However, SLD chips adapted to output light having a full width at half maximum of 150 nm or more are hard to manufacture, while their resolution is limited. By contrast, the OCT apparatus 20 enables the light outputted from the light source 30 to yield a broad full width at half maximum and exhibits a resolution of 4 μm or finer in the depth direction. Further, the degree of polarization is small, i.e., substantially zero, in fiber-type light sources such as the light source 30. Therefore, the OCT apparatus 20 can attain a tomogram with a low degree of polarization and a high resolution.

The light source 30 is widely applicable to the field of near-infrared spectroscopy without being restricted to the OCT apparatus.

Figure 10:
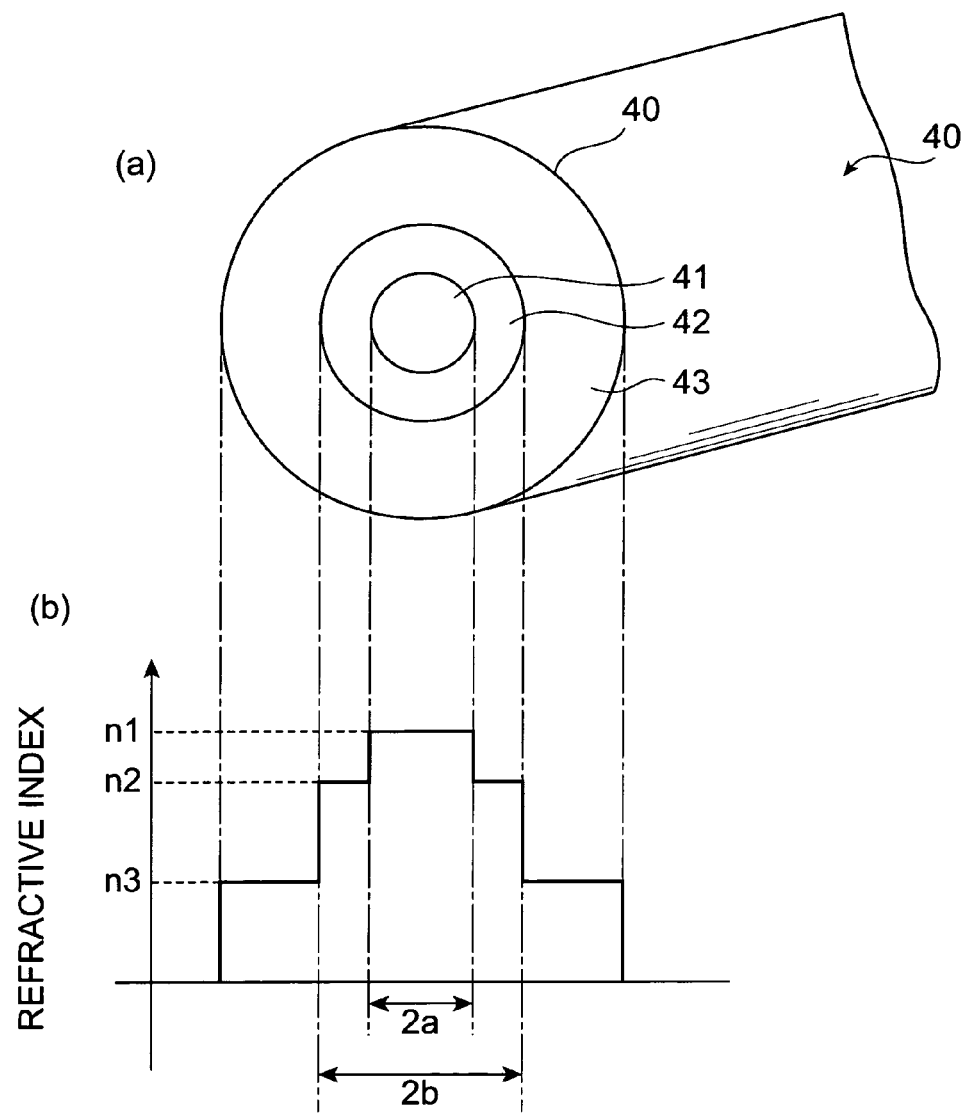
FIG. 10 is a view showing a cross-sectional structure of the optical fiber according to the present invention and its refractive index profile.
Figure 11:
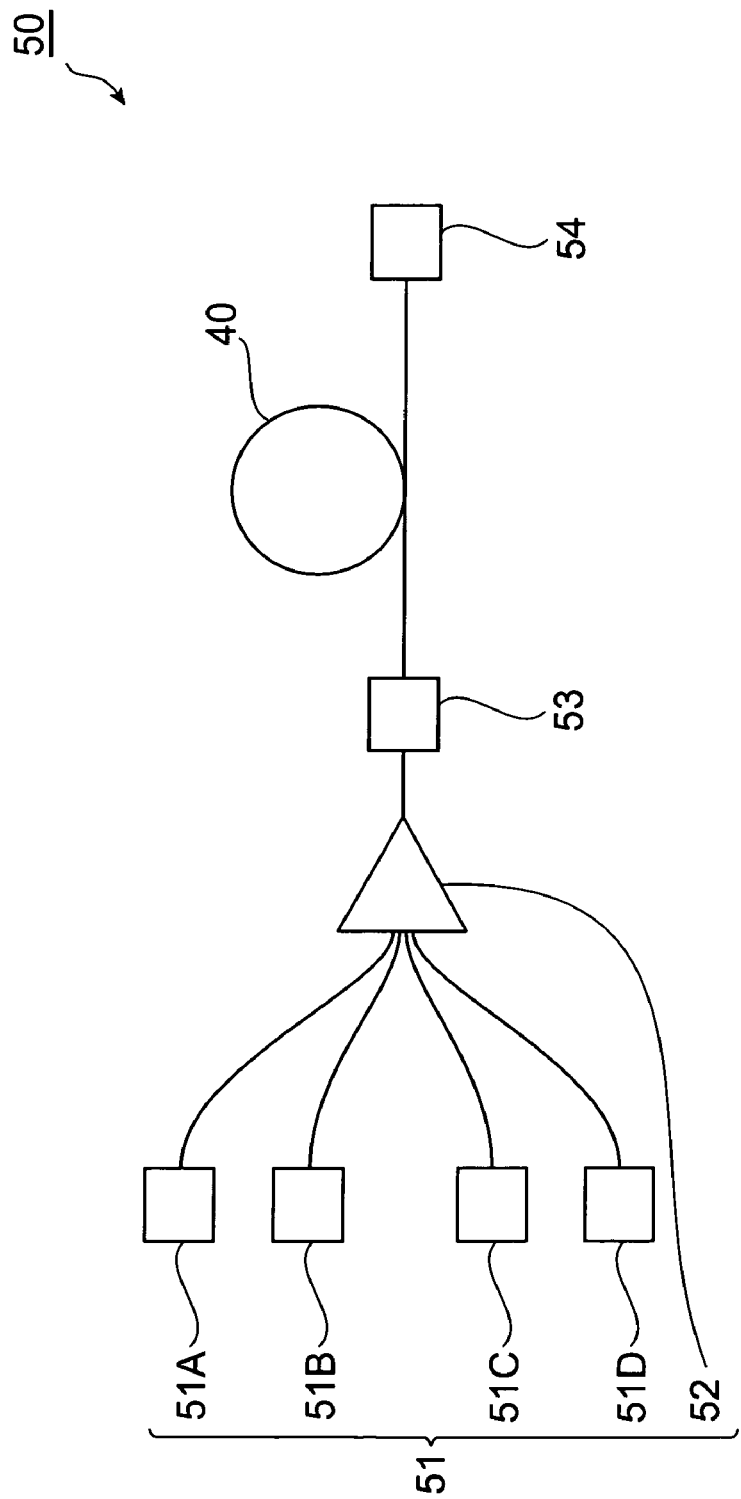
FIG. 11 is a view schematically showing the structure of an embodiment of the optical fiber laser according to the present invention.

An embodiment of the optical fiber laser according to the present invention will now be explained. FIG. 10 is a view showing the structure of an optical fiber including fluorescent glass having the structure mentioned above, in which the areas (a) and (b) show its cross-sectional structure and refractive index profile, respectively. FIG. 11 is a view schematically showing the structure of an optical fiber laser employing the optical fiber shown in FIG. 10 (the optical fiber laser according to the present invention).

As shown in the area (a) of FIG. 10, the optical fiber 40 including the fluorescent glass is a double-clad fiber comprising a core region 41 having a refractive index n1 and extending along a predetermined axis; an inner cladding region 42, provided on the outer periphery of the core region 41, having a refractive index n2 (<n1; and an outer cladding region 43, provided on the outer periphery of the inner cladding region 42, having a refractive index n3 (<n2). At least a part of the core region 41 in the optical fiber 40 is constituted by fluorescent glass having the structure mentioned above (the fluorescent glass according to the present invention). For example, in the optical fiber 40, the core region 41 has a diameter $2a$ of 20 μm and a numerical aperture NA of 0.06, whereas the inner cladding region 42 has a diameter $2b$ of 250 μm and a numerical aperture NA of about 0.4. The outer cladding region 43 is comprised of a resin, for example.

The optical fiber laser 50 shown in FIG. 11 comprises an optical fiber 40, a pumping light supplier 51, a high-reflectance fiber grating 53, and a low-reflectance fiber grating 54. In the optical fiber laser 50, the pumping light supplier 51 supplies pumping light having a predetermined wavelength to the optical fiber 40, thereby pumping a dopant contained in the optical fiber 40. The pumped dopant in the optical fiber 40 generates laser light having a wavelength different from that of the pumping light. Thus generated laser light is resonated within a resonator constructed by the high-reflectance fiber grating 53 and low-reflectance fiber grating 54, and then is emitted therefrom.

The pumping light supplier 51 includes a plurality of (4 in this embodiment) pumping LDs (laser diodes) 51A to 51D, and a pumping light multiplexer 52 to which the plurality of pumping LDs 51A to 51D are connected. The pumping LDs 51A to 51D supply the optical fiber 40 with pumping light for pumping the dopant contained in the fluorescent glass included in the core region 41 of the optical fiber 40. The pumping light multiplexer 52 multiplexes the pumping light components outputted from the plurality of pumping LDs 51A to 51D. For example, a 7×1 mutimode fiber (MMF) combiner is used as the pumping light multiplexer 52 in general. Here, the 7×1 mutimode fiber (MMF) combiner used as the pumping light multiplexer 52 is constituted by fibers whose input side is equivalent to pigtails (each having a cladding diameter of 125 μm and a core diameter of 105 μm, for example) of a pumping LD module, and is made by binding seven such fibers together and extending the resulting bundle while melting it such that a diameter conforming to the optical fiber 40 is obtained.

The optical fiber 40 is placed as a laser medium in the optical path of the resonator constructed by the high-reflectance fiber grating 53 and low-reflectance fiber grating 54. The resonator resonates the light emitted from the dopant contained in the fluorescent glass included in the core region of the optical fiber 40. The low-reflectance fiber grating 54 reflects a part of the light by a reflectance of 10% and transmits therethrough the rest of light.

In the optical fiber laser 50, the pumping light outputted from the pumping LDs 51A to 51D is supplied to the optical fiber 40 by way of the pumping light multiplexer 52. The pumping light supplied to the optical fiber 40 pumps the dopant contained in the fluorescent glass included in the core region 41 of the optical fiber 40.

When pumped with the pumping light, the dopant contained in the core region 41 of the optical fiber 40 generates spontaneous emission (fluorescence). The spontaneous emission propagates through the optical fiber 40, and travels back and forth within the resonator constructed by the high-reflectance fiber grating 53 and low-reflectance fiber grating 54. While the spontaneous emission propagates through the optical fiber 40, stimulated emission occurs, thereby generating a laser oscillation. A part of the stimulated emission is outputted as laser light from the low-reflectance fiber grating 54 to the outside.

The optical fiber includes fluorescent glass having the structure mentioned above (the fluorescent glass according to the present invention). Therefore, semiconductor lasers in the 980-nm wavelength band which are inexpensive and reliable can be used as the pumping LDs 51A to 51D when the optical fiber 40 includes fluorescent glass which is silica-based glass, adapted to generate fluorescence in response to pumping light in the 980-nm wavelength band, containing Bi as a dopant. Further, temperature control is easy, since Bi is contained.

The 980-nm wavelength band semiconductor lasers, which are inexpensive and highly reliable, can also be used as the pumping LDs 51A to 51D when the optical fiber 40 includes fluorescent glass containing at least one species of transition metal as a dopant and having a 980-nm band absorption spectrum whose full width at half maximum exceeds 10 nm. In addition, this alleviates restrictions on choosing the wavelength of the pumping light source.

When the optical fiber 40 includes fluorescent glass which is silica-based fluorescent glass containing at least one species of transition metal and exhibiting a fluorescence spectrum with a peak intensity fluctuating within a range of −1 dB or more but 1 dB or less with respect to pumping light having a fixed intensity in a state set to a temperature of −5° C. or more but 65° C. or less, its temperature dependency becomes lower, so that it can easily be put into practical use.

As in the foregoing, the optical fiber laser 50 can easily be put into practical use when equipped with the optical fiber 40 including the fluorescent glass according to the present invention.

Since the above-mentioned fluorescent glass such as fluorescent glass doped with Bi element has a wide gain spectrum, the optical fiber laser employing the fluorescent glass according to the present invention can set its laser oscillation wavelength relatively freely. The laser oscillation wavelength can be set with a higher degree of freedom by changing grating periods of the fiber gratings 53, 54.

Figure 12:
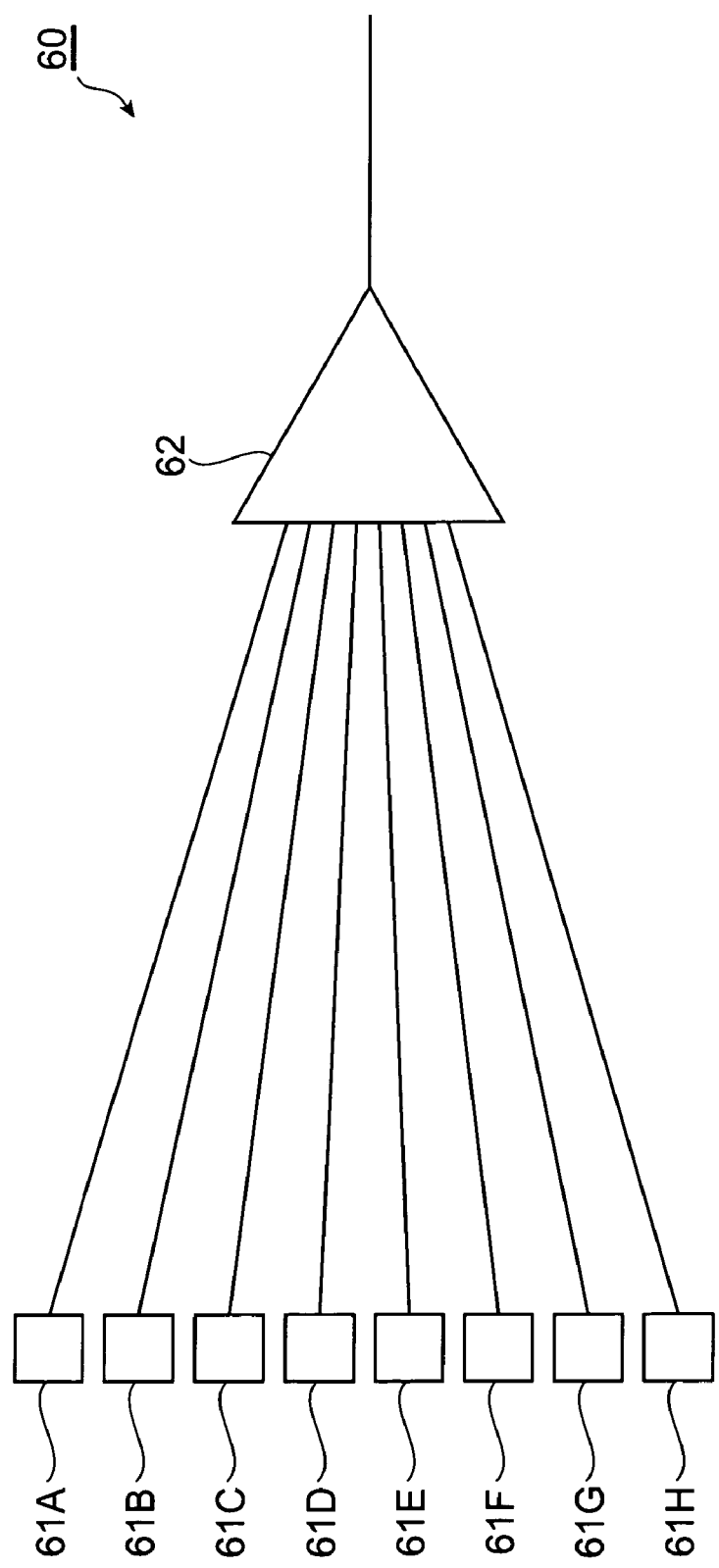
FIG. 12 is a view schematically showing the structure of a modified example of the optical fiber laser according to the present invention.
Figure 13:
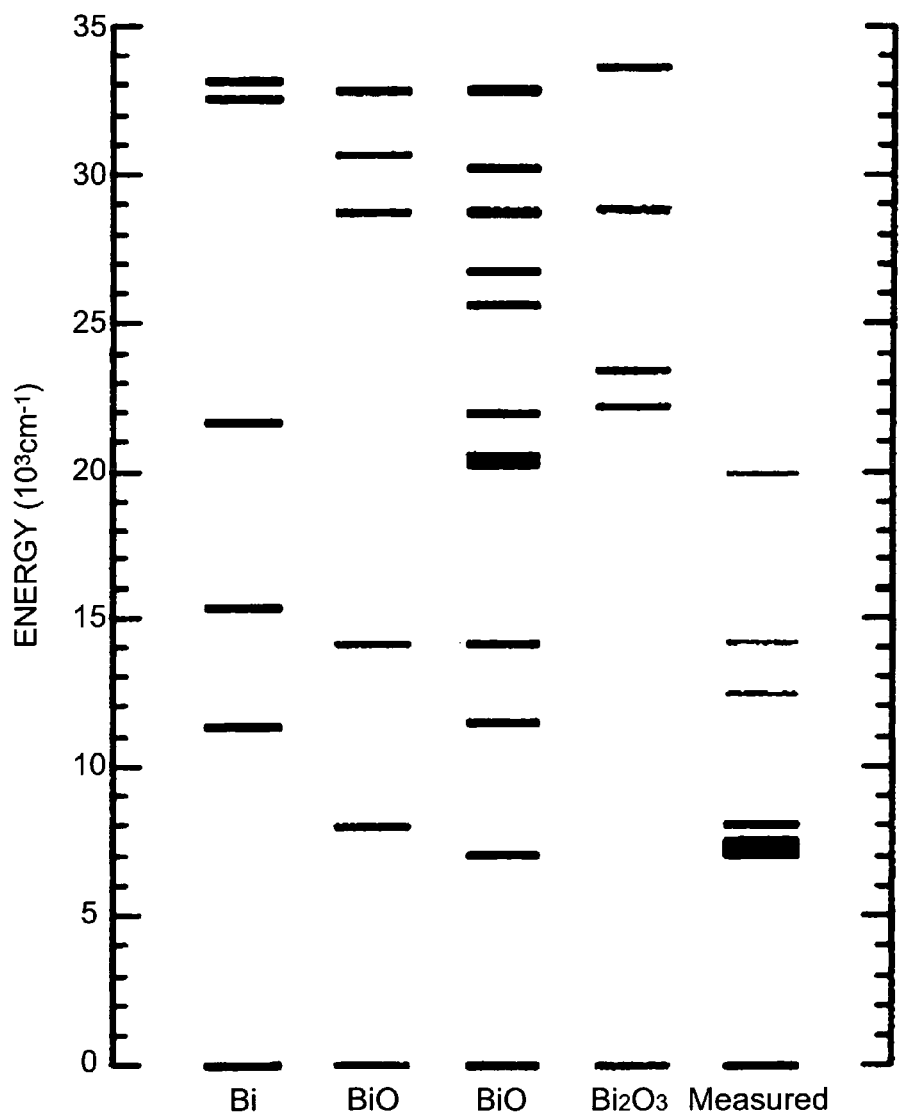
FIG. 13 is an energy level chart of Bi element ions.

Though preferred embodiments are explained in the foregoing, the present invention is not restricted to the above-mentioned embodiments and can be modified in various ways. For example, the optical fiber laser may be constructed as an optical fiber laser which multiplexes laser light beams outputted from a plurality of optical fiber lasers as shown in FIG. 12 instead of being a single unit. Specifically, the optical fiber laser 60 shown in FIG. 12 causes a WDM multiplexer 62 to multiplex laser light having an oscillation wavelength of 1040 nm emitted from an optical fiber laser 61A, laser light having an oscillation wavelength of 1060 nm emitted from an optical fiber laser 61B, laser light having an oscillation wavelength of 1080 nm emitted from an optical fiber laser 61C, laser light having an oscillation wavelength of 1100 nm emitted from an optical fiber laser 61D, laser light having an oscillation wavelength of 1120 nm emitted from an optical fiber laser 61E, laser light having an oscillation wavelength of 1140 nm emitted from an optical fiber laser 61F, laser light having an oscillation wavelength of 1160 nm emitted from an optical fiber laser 61G, and laser light having an oscillation wavelength of 1180 nm emitted from an optical fiber laser 61H, and outputs thus multiplexed laser light. In this case, the multiplexed laser light has an output which is eight times that of the individual laser light outputted from each of the optical fiber lasers 61A to 61H. A fiber-type coupler is preferably used as the WDM multiplexer 62 from the viewpoint of reliability.

Though silica-based BiDF co-doped with Al is explained as samples A and B, the present invention is also applicable to other compositions. For example, Documents 1 and 2 assume the fluorescence mechanism of Bi ions to be $Bi^{3+}$. From the energy level chart of Bi element ions shown in FIG. 13, however, the BiO (i.e., bivalent) state is presumed to be more appropriate rather than the assumption mentioned above. From FIG. 13, it seems preferable for $Bi_2O_3$ to be co-doped with a reducing agent (e.g., Sb or Sn) to such an extent that Bi is not metallized if fluorescence is seen. Such a composition may also be employed.

As in the foregoing, the present invention provides fluorescent glass, an optical waveguide, an optical fiber, an optical coherence tomography apparatus, and an optical fiber laser which can easily be put into practical use.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An optical fiber comprising:
   a core region at least partly comprised of fluorescent glass; and
   a cladding region provided on an outer periphery of said core region, wherein
   said fluorescent glass comprised of silica-based glass containing Bi as a dopant, in a fiber drawing,
   said optical fiber being rapidly cooled in which time to solidify from a molten state is 1 second or less, and
   said silica-based glass having a formation adjusted so as to output ASE (amplified spontaneous emission) light having a spectrum peak near a wavelength of 1100 nm in response to pumping light in a wavelength band of 980 nm incident thereon.

2. The optical fiber according to claim 1, wherein a wavelength of the pumping light and a peak wavelength of a spectrum of the fluorescence yield a difference of 16% or less with respect to the wavelength of the pumping light.

3. An optical coherence tomography apparatus comprising:
   a light source having the optical fiber according to claim 1, said light source amplifying fluorescence generated by said fluorescent glass when fed with pumping light and outputting ASE as amplified light;

a beam splitter for dividing the ASE outputted from said light source into first divided light advancing in a first optical path direction and second divided light advancing in a second optical path direction toward an object;

a mirror, arranged on an optical path of the first divided light and movable in parallel with the first optical path direction, for reflecting the first divided light in a direction opposite from the first optical path direction; and a photodetector for superposing the first divided light reflected by said mirror and the second divided light reflected by the object onto each other such that interference occurs within said beam splitter, and detecting thus obtained coherent light, wherein said optical coherence tomography apparatus measures a three-dimensional tomogram of the object with a resolution of 4 μm or finer in a depth direction.

4. An optical fiber laser comprising:

the optical fiber according to claim 1; and a pumping light supply part for supplying said optical fiber with pumping light for pumping the dopant contained in said optical fiber, wherein said optical fiber is arranged as a laser medium in an optical path of a resonator for resonating light emitted from the dopant.

5. The optical fiber according to claim 1, wherein the formation of said fluorescent glass is adjusted so as to exhibit a 980-nm band absorption spectrum having a full width at half maximum exceeding 10 nm.

6. The optical fiber according to claim 5, wherein the full width at half maximum of the 980-nm band absorption spectrum exceeds 50 nm.

7. An optical coherence tomography apparatus comprising:

a light source having the optical waveguide fiber according to claim 5, said light source amplifying fluorescence generated by said fluorescent glass when fed with pumping light and outputting ASE as amplified light;

a beam splitter for dividing the ASE outputted from said light source into first divided light advancing in a first optical path direction and second divided light advancing in a second optical path direction toward an object;

a mirror, arranged on an optical path of the first divided light and movable in parallel with the first optical path direction, for reflecting the first divided light in a direction opposite from the first optical path direction; and a photodetector for superposing the first divided light reflected by said mirror and the second divided light reflected by the object onto each other such that interference occurs within said beam splitter, and detecting thus obtained coherent light, wherein said optical coherence tomography apparatus measures a three-dimensional tomogram of the object with a resolution of 4 μm or finer in a depth direction.

8. The optical fiber according to claim 1, wherein said fluorescent glass exhibits a fluorescence spectrum with a peak intensity fluctuating within a range of −1 dB or more and 1 dB or less with respect to pumping light having a fixed intensity in a state set to a temperature of −5° C. or more and 65° C. or less.

9. An optical fiber laser comprising:

the optical fiber according to claim 5; and a pumping light supply part for supplying said optical fiber with pumping light for pumping the dopant contained in said optical fiber, wherein said optical fiber is arranged as a laser medium in an optical path of a resonator for resonating light emitted from the dopant.

10. An optical coherence tomography apparatus comprising:

a light source having the optical fiber according to claim 8, said light source amplifying fluorescence generated by said fluorescent glass when fed with pumping light and outputting ASE as amplified light;

a beam splitter for dividing the ASE outputted from said light source into first divided light advancing in a first optical path direction and second divided light advancing in a second optical path direction toward an object;

a mirror, arranged on an optical path of the first divided light and movable in parallel with the first optical path direction, for reflecting the first divided light in a direction opposite from the first optical path direction; and a photodetector for superposing the first divided light reflected by said mirror and the second divided light reflected by the object onto each other such that interference occurs within said beam splitter, and detecting thus obtained coherent light, wherein said optical coherence tomography apparatus measures a three-dimensional tomogram of the object with a resolution of 4 μm or finer in a depth direction.

* * * * *